United States Patent
Cialdea et al.

(10) Patent No.: US 10,679,736 B2
(45) Date of Patent: *Jun. 9, 2020

(54) IMAGE SHARING SYSTEM

(71) Applicant: AWARE, INC., Bedford, MA (US)

(72) Inventors: James Giulio Cialdea, Woburn, MA (US); Alexis Tzannes, Lexington, MA (US); Adrian Gropper, Watertown, MA (US)

(73) Assignee: AWARE, INC., Bedford, MA (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/156,635

(22) Filed: Oct. 10, 2018

(65) Prior Publication Data

US 2019/0080787 A1 Mar. 14, 2019

Related U.S. Application Data

(63) Continuation of application No. 15/403,756, filed on Jan. 11, 2017, now Pat. No. 10,127,621, which is a (Continued)

(51) Int. Cl.
*G06F 21/62* (2013.01)
*G16H 10/40* (2018.01)
(Continued)

(52) U.S. Cl.
CPC ............ *G16H 10/40* (2018.01); *G06F 19/00* (2013.01); *G06F 19/321* (2013.01);
(Continued)

(58) Field of Classification Search
CPC ....... H04L 63/04; H04L 51/08; G06F 19/321; G06F 19/322; G06Q 50/24
(Continued)

(56) References Cited

U.S. PATENT DOCUMENTS 6,757,898 B1   6/2004   Ilsen et al.
7,949,545 B1   5/2011   Madras et al.
(Continued)

FOREIGN PATENT DOCUMENTS

JP   2005-045630   2/2005
JP   2005-045630   5/2005
(Continued)

OTHER PUBLICATIONS

Notice of Preliminary Rejection (Including Translation) for Korean Patent Application No. 10-2015-7016149, dated Aug. 23, 2019.
(Continued)

*Primary Examiner* — Matthew T Henning
(74) *Attorney, Agent, or Firm* — Jason H. Vick; Sheridan Ross, PC

(57) ABSTRACT

A server system for distributing information securely includes a network interface for receiving, over a network, an information object accompanied by metadata. A repository stores the information object. Metadata is mapped to electronic addresses of trusted recipients. A processor is configured to generate a link for accessing the information object in the repository, acquire an electronic address of a trusted recipient based on the metadata accompanying the information object, insert the link into an electronic message addressed to the electronic address of the trusted recipient, and send the electronic message with the link to the trusted recipient. The processor is further configured to receive, over a second network, a request for the information object sent from a user device in response to an activation of the link, retrieve the information object from the repository, and transmit the information object to a browser of the user device over the second network.

26 Claims, 3 Drawing Sheets

Related U.S. Application Data continuation of application No. 14/440,944, filed as application No. PCT/US2013/070473 on Nov. 18, 2013, now Pat. No. 9,548,968.

(60) Provisional application No. 61/727,856, filed on Nov. 19, 2012, provisional application No. 61/728,301, filed on Nov. 20, 2012.

(51) Int. Cl.
| | | |
|---|---|---|
| *G16H 10/60* | (2018.01) | |
| *G06F 21/60* | (2013.01) | |
| *G06F 19/00* | (2018.01) | |
| *G06Q 50/24* | (2012.01) | |
| *H04L 12/58* | (2006.01) | |
| *H04L 29/06* | (2006.01) | |
| *G16H 30/20* | (2018.01) | |

(52) U.S. Cl.
CPC ........ *G06F 21/606* (2013.01); *G06F 21/6245* (2013.01); *G06Q 50/24* (2013.01); *G16H 10/60* (2018.01); *G16H 30/20* (2018.01); *H04L 51/08* (2013.01); *H04L 63/04* (2013.01)

(58) Field of Classification Search
USPC .......................................................... 726/26
See application file for complete search history.

(56) References Cited

U.S. PATENT DOCUMENTS

| | | | |
|---|---|---|---|
| 8,478,842 B2 | 7/2013 | Holmes et al. | |
| 8,489,410 B2 | 7/2013 | Rothpearl et al. | |
| 8,543,421 B2 | 9/2013 | Menschik et al. | |
| 8,571,280 B2 | 10/2013 | Matthew | |
| 9,235,605 B2 | 1/2016 | Westin et al. | |
| 9,548,968 B2 | 1/2017 | Cialdea et al. | |
| 2002/0161775 A1 | 10/2002 | Lasensky et al. | |
| 2004/0230644 A1* | 11/2004 | Aratake .................. | H04L 51/12 709/201 |
| 2007/0239489 A1 | 10/2007 | Masuzawa et al. | |
| 2008/0147860 A1 | 6/2008 | Edwards et al. | |
| 2009/0150675 A1 | 6/2009 | Cook | |
| 2009/0228303 A1 | 9/2009 | Faulkner et al. | |
| 2009/0296540 A1 | 12/2009 | Gilbert et al. | |
| 2010/0011087 A1 | 1/2010 | Hofsetter et al. | |
| 2010/0082370 A1 | 4/2010 | Frederick et al. | |
| 2011/0087652 A1 | 4/2011 | Westin et al. | |
| 2012/0159164 A1 | 6/2012 | Brown et al. | |
| 2012/0197660 A1 | 8/2012 | Prodanovich | |
| 2012/0197664 A1 | 8/2012 | Maresh et al. | |
| 2012/0278100 A1 | 11/2012 | Macoviak | |
| 2017/0124674 A1 | 5/2017 | Cialdea et al. | |

FOREIGN PATENT DOCUMENTS

| | | |
|---|---|---|
| JP | 2006-172131 | 6/2006 |
| JP | 2008-077610 | 4/2008 |
| JP | 2011-128661 | 6/2011 |
| KR | 10-2012-0091209 | 8/2012 |

OTHER PUBLICATIONS

Decision of Final Rejection (Including Translation) for Japanese Patent Application No. 2015-542861 dated Oct. 15, 2018.
Office Action for European Application No. 13855324.3, dated May 22, 2019.
"The Direct Project Overview" Oct. 11, 2010.
Whitby, Jonathan "White Paper—The DICOM Standard" BARCO n.v., Kortrijk, Belgium, 2007.
International Search Report for International Patent Application No. PCT/US2013/070473, dated Mar. 5, 2014.
Written Opinion for International Patent Application No. PCT/US2013/070473, dated Mar. 5, 2014.
International Preliminary Report on Patentability for International Patent Application No. PCT/US2013/070473, dated May 28, 2015.
European Search Report for European Application No. 13855324.3, dated Jun. 22, 2016.
Notification of Reasons for Refusal (Including Translation) for Japanese Patent Application No. 2015-542861 dated Sep. 11, 2017.
Notification of Reasons for Refusal (Including Translation) for Japanese Patent Application No. 2015-542861 dated Mar. 19, 2018.
Office Action for U.S. Appl. No. 14/440,944, dated May 19, 2016.
Notice of Allowance for U.S. Appl. No. 14/440,944, dated Oct. 11, 2016.
Office Action for U.S. Appl. No. 15/403,756, dated Jan. 10, 2018.
Notice of Allowance for U.S. Appl. No. 15/403,756, dated Jul. 12, 2018.

\* cited by examiner

IMAGE SHARING SYSTEM

RELATED APPLICATIONS

This application is a Continuation of U.S. patent application Ser. No. 15/403,756, filed Jan. 11, 2017, now U.S. Pat. No. 10,127,621, which is a Continuation of U.S. patent application Ser. No. 14/440,944, filed May 6, 2015, now U.S. Pat. No. 9,548,968, which is a national stage application under 35 U.S.C. 371 of PCT Application No. PCT/US2013/070473, having an international filing date of Nov. 18, 2013, which designated the United States, which PCT application claims the benefit of and priority to U.S. Provisional Application No. 61/727,856, filed Nov. 19, 2012, titled "Image Sharing", and U.S. Provisional Application No. 61/728,301, filed Nov. 20, 2012, titled "Image Sharing System", the entireties of which applications are incorporated by reference herein.

FIELD OF THE INVENTION

The invention relates generally to systems and methods for securely sharing images.

BACKGROUND

The sharing of electronic health records (EHRs) and personal health records (PHRs) can provide many benefits for health care providers and their patients. With the sharing of EHRs and PHRs, health care generally improves. The sharing of EHRs and PHRs leads to complete and accurate information, improved access to such information, and empowerment of the patient, who can take an active role in their health by receiving electronic copies of their medical records. Within a radiological environment, for instance, the Digital Imaging Communications in Medicine (DICOM) standard was developed to promote communication of digital image information. The DICOM standard defines the structure of radiological objects, such as images, reports, measurements and other patient documentation, and the manner in which such radiological objects are exchanged. However, before one can fully reap the benefits of electronically sharing EHRs, any system designed to exchange medical records needs to take into consideration that such records contain highly confidential and sensitive information.

To help protect the highly confidential and sensitive nature of exchanged health information among healthcare participants, the Office of the National Coordinator for Health Information Technology developed the Direct Secure Messaging (Direct) standards. In brief, Direct is a secure electronic communication service by which health care personnel can send authenticated, encrypted health information directly to known, trusted recipients. Direct operates like electronic mail (email) with security features, such as point-to-point encryption.

SUMMARY

In one aspect, the invention features a server system for securely distributing information. The server system comprises a network interface receiving, over a network, an information object accompanied by metadata. A repository stores the information object. Mapping means maps metadata to electronic addresses of trusted recipients. A processor is configured to generate a link for accessing the information object in the repository, to acquire an electronic address of a trusted recipient from the lookup table based on the metadata accompanying the received information object, to insert the link into an electronic message addressed to the electronic address of the trusted recipient, and to send the electronic message with the link to the electronic address of the trusted recipient.

In another aspect, the invention features a method of securely distributing information. The method comprises receiving, over a network, an information object accompanied by metadata. The information object is stored in a repository. A link is generated for accessing the information object in the repository. The metadata accompanying the information object is mapped to an electronic address of a trusted recipient. The link is inserted into an electronic message, and the electronic message with the link is securely sent to the electronic address of the trusted recipient.

In still another aspect, the invention features a computer program product for distributing information securely. The computer program product comprises a computer readable non-transitory storage medium having computer readable program code embodied therewith. The computer readable program code comprises computer readable program code that, if executed, receives an information object accompanied by metadata over a network; computer readable program code that, if executed, stores the information object in a repository; computer readable program code that, if executed, generates a link for accessing the information object in the repository; computer readable program code that, if executed, maps the metadata accompanying the information object to an electronic address of a trusted recipient; computer readable program code that, if executed, inserts the link into a secure electronic message; and computer readable program code that, if executed, sends the secure electronic message with the link to the electronic address of the trusted recipient.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Image-sharing servers described herein facilitate secure streaming and viewing of images. Such image-sharing servers can be part of an electronic health record (EHR) system used to share medical images in a manner that qualifies as "Meaningful Use" both inside and outside of an institution, such as a healthcare facility. In general, "Meaningful Use" refers to a set of standards, defined by the Centers for Medicare & Medicaid Services (CMS) Incentive Programs governing the use of electronic health records. Healthcare providers that meet specific criteria become eligible to earn incentive payments. Meaningful Use objectives have three stages with various criteria. Meaningful Use Stage 2 (MU2) criteria include rigorous health information exchange (HIE) and the electronic transmission of patient care summaries across multiple settings.

The aforementioned secure messaging system, Direct, has a shortcoming in that the Direct standards do not accommodate the attachment of large files (e.g., 1 GB, 2 GB) or payloads that change continuously to a secure electronic message. This presents a limitation to the sharing of those EHRs that include one or more sizable images or studies (i.e., series of images) or have continuously changing data, such as that produced by physiologic monitors (e.g., implantable cardiac defibrillators). The image-sharing servers described herein provide a mechanism by which such images can be securely acquired over a different pathway or channel from that taken by the secure messages, thereby avoiding the attachment size limitation of the secure messaging system, while still satisfying the MU2 criteria.

In brief overview, the embodiments of image-sharing servers described herein receive and store protected resources, such as an image, or series of images, and generate links for accessing such protected resources. The link is included in a secure (e.g., Direct) email message and sent with an MU2 EHR to a trusted recipient, for example, a staff member. The trusted recipient can then forward the email with the link to another person, using a second secure email message. The original and second secure email message resides in MU2-compliant inboxes awaiting viewing. When a recipient activates the link, the image-sharing server streams the associated image or series of images to the browser of the recipient's device. Any electronic device with a browser can serve to view the images. The streaming of each image can occur using a secure communication protocol, such as https.

Figure 1:
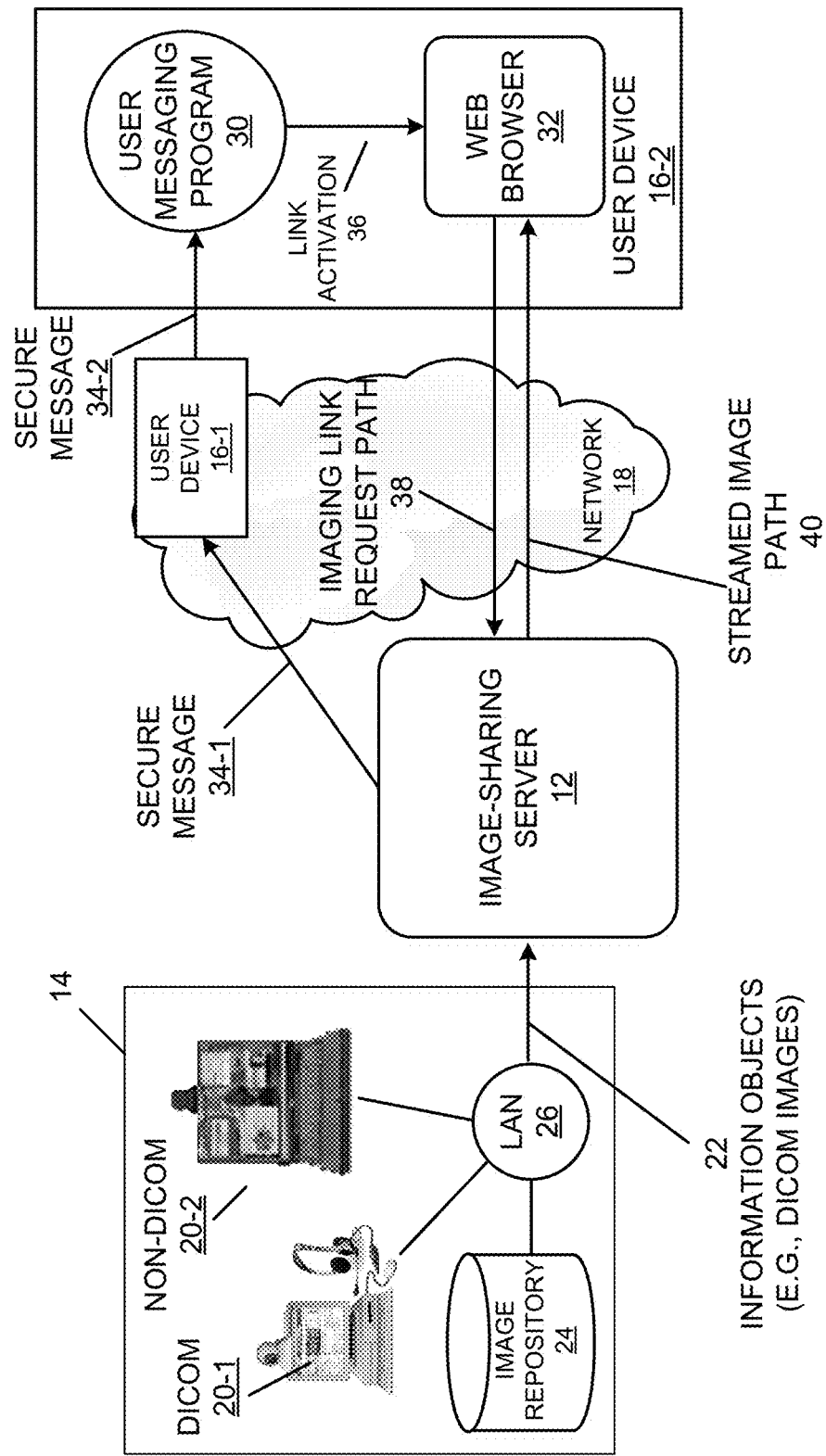
FIG. 1 is a diagram of an embodiment of a secure image-sharing system including an image-sharing server system in communication between a healthcare facility and a plurality of user devices.

FIG. 1 shows an embodiment of a secure image-sharing system 10 including an image-sharing server system 12 in communication with an enterprise 14, such as a healthcare facility, and with a plurality of user devices 16-1, 16-2 (generally, user device 16) over a network 18. Although shown external to the enterprise 14, the image-sharing server system 12 can be part of the enterprise 14.

The enterprise 14 includes one or more sources 20-1, 20-2 (generally, source 20) of information objects 22 (that is, secure objects, e.g., images, image series, and structured reports) and a repository 24 coupled to a local network (e.g., a LAN, TCP/IP, Ethernet) 26 for storing the information objects 22. Each source 20 can be any electronic equipment capable of capturing and transferring images over the network 26, for example, a radiological or computerized tomography (CT) scanning system. For illustration purposes, the source 20-1 produces information objects 22 in accordance with the DICOM (Digital Imaging and Communications in Medicine) standard used to handle, store, and transmit medical images and associated imaging information, whereas the source 20-2 produces non-DICOM secure objects, for example, pathology images.

In one embodiment, the sources 20, repository 24, and network 26 are part of a DICOM network, which can include other networked devices (not shown), such as CT and computed radiography (CR) scanners to create and send images, a Picture Archiving and Communication System (PACS) to handle the archiving and distribution of images and related objects, and reporting and post-processing workstations.

The image-sharing server system 12 comprises one or more computing systems configured to acquire information objects 22 from the enterprise 14, and automatically generate and securely send links to the information objects to trusted users. These trusted users can use their user devices 16-1 to access and view the information objects 22, or, forward the automatic notification with the link to other persons, who may use their user devices 16-2 to access and view the information objects 22.

In general, each user device 16 is an electronic device capable of receiving electronic messages and connecting to servers and other devices over the network 18 using, for example, a web browser program. As a representative example of the user devices 16, the user device 16-2 includes a user-messaging application program 30 and a web browser program 32. The user-messaging application 30 can be any commercially available electronic mail program, for example, Microsoft Outlook™. The web browser program 32 can be any commercially available Web browser, for example Microsoft INTERNET EXPLORER®, Mozilla FIREFOX®, NETSCAPE®, Opera Software OPERA™, and Apple SAFARI®. (Currently, most computing devices already have an installed browser when purchased from a manufacturer and deployed in the business, enterprise, or home). No browser add-ons or extensions are needed for the user device 16-2 to request and receive the information objects 22 from the image-sharing server system 12 as described herein. Example implementations of the user device 16-2 include, but are not limited to, electronic tablets or notepads (e.g., iPAD™), personal computers (PC), Macintosh computers, workstations, laptop computers, kiosks, hand-held devices, such as a personal digital assistants (PDAs), mobile smart phones (e.g., iPHONE™, BlackBerry™), navigation and global positioning systems, and network terminals.

Embodiments of the network 18 include, but are not limited to, local-area networks (LAN), metro-area networks (MAN), and wide-area networks (WAN), such as the Internet or World Wide Web. Each user device 16 can connect to the image-sharing server system 12 over the network 18 through one of a variety of connections, such as standard telephone lines, digital subscriber line (DSL), asynchronous DSL, LAN or WAN links (e.g., T1, T3), broadband connections (Frame Relay, ATM, X.25), and wireless connections (e.g., 802.11(a), 802.11(b), 802.11(g), 802.11(n)).

In brief overview, information objects 22 pass to the image-sharing server system 12 over the network 26. In response to receiving an information object 22 (e.g., image or series of images), the image-sharing server system 12 automatically stores the information object 22, creates a link (e.g., a Universal Resource Locator or URL) associated with the information object 22, and generates a secure message 34-1 that includes the link, and, typically, a health record. The image-sharing server system 12 maintains a record of each link generated and the one or more secure information objects 22 associated with the link. Such records can reside within a database at the image-sharing server system.

The image-sharing server system 12 sends this first secure message 34-1 to a known, trusted recipient (e.g., a staff member) with, for example, an MU2 EHR (Meaningful Use Stage 2 Electronic Health Record) status. As a result, this automated secure message 34-1 is placed completely under the control of the receiving institution, giving the receiving institution administrative control (e.g., department-by-department) of message routing. The known, trusted recipient may then forward the link (along with a health record conveyed by the first secure message) to others (e.g., a clinician, referring physician, or patient that can be reached by user device 16-2) in a second secure message 34-2. The second user, who is the destination of the forwarded message 34-2, may have a completely different trust relationship with the enterprise 14, the originator of the images, from the first user who receives the automatic notification 34-1 based on metadata (as described in more detail).

Secure messages 34-1, 34-2 include, but are not limited to, email messages and instant messages. In one embodiment, the secure messages 34-1, 34-2 are Direct Project (or simply Direct) messages. Direct messages are secure email-like communications containing health or medical data, authenticated, encrypted, and transmitted to known, trusted individuals over a network in accordance with the Direct Project specifications provided by the Direct Project (direct-project.org).

The forwarded secure message 34-2 appears in the user's secure (e.g., MU2-compliant) inbox. When the user, by way of the user device 16-2, activates the link in the message 34-2, the activation 36 can launch the web browser 32 installed on the user device 16-2 (if not already running), and the web browser 32 may use a hypertext transfer protocol (HTTP, HTTPS) to request the secure information object 22 from the image-sharing server system 12 at the location indicated by the link.

The request traverses a communication path 38 through the network 18 to arrive at the image-sharing server system 12. In response to the request, the image-sharing server system 12 acquires the information objects signified by the link, such as files and images. The image-sharing server system 12 then transmits the information objects over a communication path 40 to the web browser 32 running on the user device 16-2. In one embodiment, the image-sharing server system 12 streams the acquired images over the communication path 40 to the web browser 32 running on the user device 16-2.

Various security processes can secure the URL link used to view images, including, but not limited to, encrypting the communications over the path 40 using SSL and TLS, short-term expiration of the URL to avoid interception and reuse, and single-sign-on federated authentication and authentication challenge (e.g. password or token such as OAuth token) prior to serving information via the URL. The same or similar security processes may be used to secure the streaming of the images to the requesting user device 16.

Figure 2:
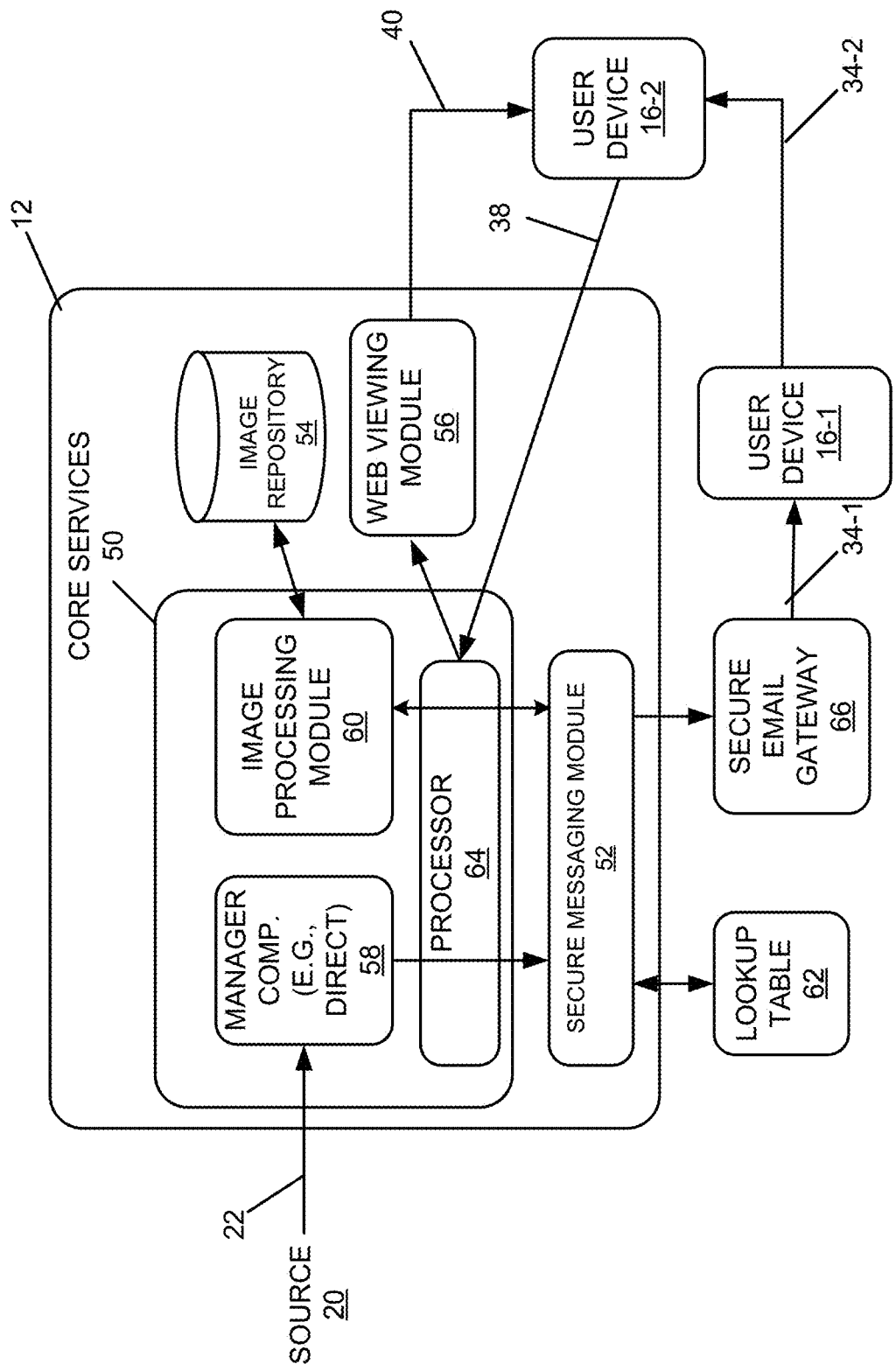
FIG. 2 is a diagram of an embodiment of the image-sharing server system comprised of a core services module, a secure messaging module, an image repository, and a Web communication module.

FIG. 2 shows an embodiment of the image-sharing server system 12 comprised of a core services module 50, a secure messaging module 52, an image repository 54, and a Web communication module 56. The distribution of the links, as described herein, occurs in near real time; the image-sharing server system 12 operates to distribute secure email messages, containing links to images, to known, authorized recipients as those images arrive at the image-sharing server system 12.

The core services module 50 includes a manager component 58 configured to receive information objects 22 (e.g., DICOM and non-DICOM imaging studies) from a source 20, and an image-processing module 60 configured to process and prepare images for streaming (e.g., according to JPEG2000), and to store such images in the image repository 54.

The secure messaging module 52 is in communication with a lookup table 62 that contains a mapping of metadata to secure email addresses. The lookup table 62 is an embodiment of a means for mapping metadata to secure email addresses to trusted recipients. Other embodiments of such means for mapping include, but not limited to, hash tables, linked lists, and search trees.

In one embodiment the lookup table 62 maps AE (application entity) titles to email addresses. According to the DICOM standard, every node or device in a DICOM network has an AE title, that is, a name used to identify a DICOM service on the node or device. Different AE titles can be used for each DICOM operation. Received DICOM information objects include metadata, such as an AE title associated with the DICOM information object. Similar to the AE titles of DICOM information objects, non-DICOM information objects can have identifying metadata that the lookup table 62 can map to secure email addresses.

The secure messaging module 52 is also in communication with a secure email gateway 66, and is configured to generate a link (e.g., a URL) for a given object and send the link to this secure email gateway 66 in a secure email. In one embodiment, the secure messaging module 52 is configured to operate in accordance with the Direct project specifications. When working with non-DICOM information objects, the image-sharing server system 12 operates generally as an adapter from any non-DICOM protocol to a Direct or Direct-like communications protocol.

The Web viewing module 56 is configured to stream images to user devices 16 in response to requests received over the network 18.

Figure 3:
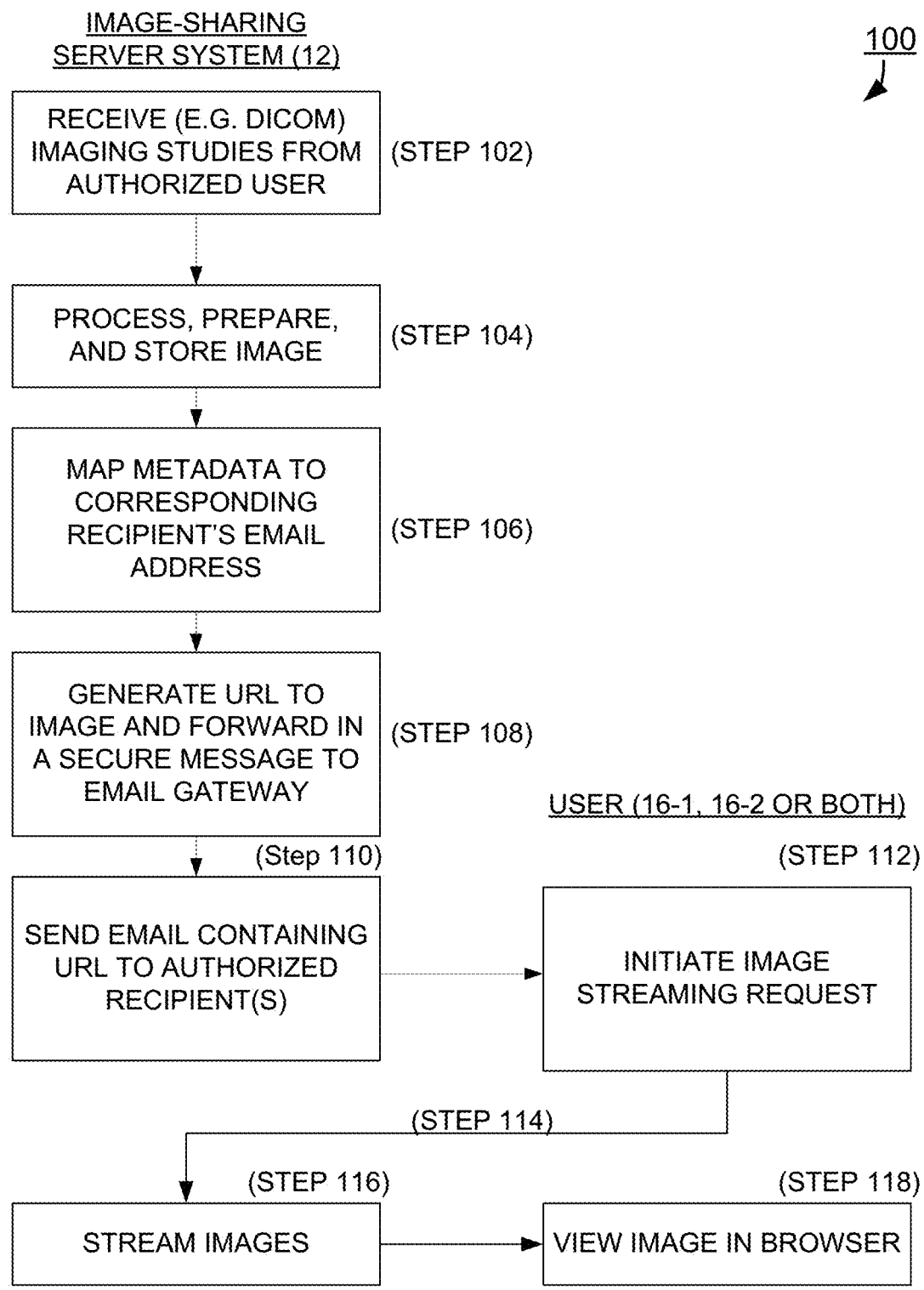
FIG. 3 is a flow diagram of an embodiment of a process for securely distributing studies and images to a known, trusted recipient.

FIG. 3 shows an embodiment of a process 100 for securely distributing studies and images to known, trusted personnel. In this description of the process 100, reference is also made to elements of FIG. 1 and FIG. 2. At step 102, the manager component 58 receives an information object 22 (e.g., a DICOM or non-DICOM study, image, or series of images) from an authorized source 20. The processor 64 directs the image-processing module 60 to acquire (step 104) the information objects 22 from the manager component 58. The image-processing module 60 processes and prepares each information object 22 for streaming, and stores the result in the image repository 54.

The processor 64 directs the secure messaging module 52 to obtain metadata (e.g., an AE title) from the received information object 22, and to use the lookup table 62 to map (step 106) the metadata to an authorized recipient's (e.g., Direct) secure email address. The secure messaging module 52 also generates (step 108) a URL (i.e., a link) for accessing the particular information object 22 stored in the image repository 54 and an email message with the URL, and sends the email message to the secure message gateway 66. The secure message gateway 66 sends (step 110) the secure email message 34-1 containing the URL to the authorized recipient's email address.

In this example, the authorized recipient uses the user device 16-1 to receive and forward the secure email message 34-1 to the secure email address of another recipient. This second secure email message 34-2 contains the link and, usually, a protected resource, such as a health record. Alternatively, or in addition, the authorized recipient can activate the link in the first secure email message 34-1 to receive the information object 22 from the image-sharing server system 12.

The user device 16-2 of the second recipient receives and opens the forwarded secure email message 34-2 with the link using the client-side user-messaging program 30. When the second recipient activates (step 112) the link in the secure email message 34-2, the web browser 32 launches (if not already open) and sends (step 114) a request 38 to the core services module 50 of the image-sharing server system 12. In response to the request 38, the processor 64 directs the image-processing module 60 to acquire and return, for example, the image or images associated with the link from the image repository 54. The processor 64 then directs the Web viewing module 56 to stream (step 116) the image or series of images to the user device 14. The user views (step 118) the image within the browser 22 running on the device 14.

As will be appreciated by one skilled in the art, aspects of the present invention may be embodied as a system, method, and computer program product. Thus, aspects of the present invention may be embodied entirely in hardware, entirely in software (including, but not limited to, firmware, program code, resident software, microcode), or in a combination of hardware and software. All such embodiments may generally be referred to herein as a circuit, a module, or a system. In addition, aspects of the present invention may be in the form of a computer program product embodied in one or more computer readable media having computer readable program code embodied thereon.

Any combination of one or more computer readable medium(s) may be utilized. The computer readable medium may be a computer readable signal medium or a computer readable storage medium. The computer readable medium may be a non-transitory computer readable storage medium, examples of which include, but are not limited to, an electronic, magnetic, optical, electromagnetic, infrared, or semiconductor system, apparatus, or device, or any suitable combination thereof.

As used herein, a computer readable storage medium may be any tangible medium that can contain or store a program for use by or in connection with an instruction execution system, apparatus, device, computer, computing system, computer system, or any programmable machine or device that inputs, processes, and outputs instructions, commands, or data. A non-exhaustive list of specific examples of a computer readable storage medium include an electrical connection having one or more wires, a portable computer diskette, a floppy disk, a hard disk, a random access memory (RAM), a read-only memory (ROM), a USB flash drive, an non-volatile RAM (NVRAM or NOVRAM), an erasable programmable read-only memory (EPROM or Flash memory), a flash memory card, an electrically erasable programmable read-only memory (EEPROM), an optical fiber, a portable compact disc read-only memory (CD-ROM), a DVD-ROM, an optical storage device, a magnetic storage device, or any suitable combination thereof.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. As used herein, a computer readable storage medium is not a computer readable signal medium or a propagated signal.

Program code may be embodied as computer-readable instructions stored on or in a computer readable storage medium as, for example, source code, object code, interpretive code, executable code, or combinations thereof. Any standard or proprietary, programming or interpretive language can be used to produce the computer-executable instructions. Examples of such languages include C, C++, Pascal, JAVA, BASIC, Smalltalk, Visual Basic, and Visual C++.

Transmission of program code embodied on a computer readable medium can occur using any appropriate medium including, but not limited to, wireless, wired, optical fiber cable, radio frequency (RF), or any suitable combination thereof.

The program code may execute entirely on a user's computer, partly on the user's computer, as a stand-alone software package, partly on the user's computer and partly on a remote computer or entirely on a remote computer or server. Any such remote computer may be connected to the user's computer through any type of network, including a local area network (LAN) or a wide area network (WAN), or the connection may be made to an external computer (for example, through the Internet using an Internet Service Provider).

In addition, the described methods may be implemented on an image-processing device, or the like, or on a separate programmed general-purpose computer having image processing capabilities. Additionally, the methods of this invention can be implemented on a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device such as PLD, PLA, FPGA, PAL, or the like. In general, any device capable of implementing a state machine that is in turn capable of implementing the proposed methods herein can be used to implement the image-processing system according to this invention.

Furthermore, the disclosed methods may be readily implemented in software using object or object-oriented software development environments that provide portable source code that can be used on a variety of computer or workstation platforms. Alternatively, the disclosed system may be implemented partially or fully in hardware using standard logic circuits or a VLSI design. Whether software or hardware is used to implement the systems in accordance with this invention is dependent on the speed and/or efficiency requirements of the system, the particular function, and the particular software or hardware systems or microprocessor or microcomputer systems being utilized. The methods illustrated herein however can be readily implemented in hardware and/or software using any known or later developed systems or structures, devices and/or software by those of ordinary skill in the applicable art from the functional description provided herein and with a general basic knowledge of the computer and image processing arts.

Moreover, the disclosed methods may be readily implemented in software executed on programmed general-purpose computer, a special purpose computer, a microprocessor, or the like. In these instances, the systems and methods of this invention can be implemented as program embedded on personal computer such as JAVA® or CGI script, as a resource residing on a server or graphics workstation, as a plug-in, or the like. The system can also be implemented by physically incorporating the system and method into a software and/or hardware system, such as the hardware and software systems of an image processor.

What is claimed is:

1. A server system configured to securely distribute information comprising:
   a network interface and image sharing server receiving an information object accompanied by metadata, the metadata identifying one or more trusted recipients;

a repository, in communication with the image sharing server, storing the information object;

computer instructions that automatically map the metadata to one or more electronic addresses of the one or more trusted recipients;

a processor configured to generate a universal resource locator for accessing the information object stored in the repository, and to acquire the one or more electronic addresses of the trusted recipients based on the metadata accompanying the received information object;

the processor in conjunction with a secure messaging module inserting the universal resource locator into an electronic message addressed to the one or more electronic addresses of the trusted recipients, and sending the electronic message, using a secure email gateway, with the universal resource locator, to the one or more electronic addresses of the trusted recipients, the electronic message being secure and sent with a MU2 EHR status including administrative control, wherein the universal resource locator in the electronic message is selectable by a user to access the information object via a web browser;

the image sharing server:
receiving, in response to the selection of the universal resource locator, a request for the information object based on the universal resource locator in the electronic message, acquiring the information object signified by the universal resource locator, and providing the information object over a communications path for display on a web browser, wherein the providing of the information object over the communications path occurs over a different pathway or channel than the electronic message to avoid an attachment size limitation.

2. The server system of claim 1, wherein the processor is further configured to generate the universal resource locator and send the electronic message with the universal resource locator automatically in response to the network interface receiving the information object accompanied by the metadata.

3. The server system of claim 1, wherein the processor is further configured to:
receive, over a second network, a request for the information object sent from a user device in response to an activation of the universal resource locator; retrieve the information object from the repository; and transmit the information object to a browser of the user device over the second network.

4. The server system of claim 3, wherein the processor is further configured to transmit a series of information objects in response to the request prompted by the activation of the universal resource locator.

5. The server system of claim 1, wherein the information object is an image or a study.

6. The server system of claim 1, wherein the electronic message is a Direct Project (Direct) secure email message.

7. The server system of claim 1, wherein the network includes a Digital Imaging Communications in Medicine (DICOM) network.

8. The server system of claim 1, wherein the metadata accompanying the information object includes an application entity (AE) title.

9. A method of securely distributing information comprising:

receiving, over a network and using a network interface, an information object, at an image sharing server, accompanied by metadata, the metadata identifying a trusted recipient;

storing the information object in a repository, the repository in communication with the image sharing server;

automatically generating, using computer instructions, a universal resource locator for accessing the information object stored in the repository;

automatically mapping, using computer instructions, the metadata accompanying the information object to an electronic address of the trusted recipient;

automatically inserting, using a processor, the universal resource locator into a secure electronic message addressed to the electronic address of the trusted recipient;

automatically sending the secure electronic message, using a secure email gateway and processor, with the universal resource locator to the electronic address of the trusted recipient, the electronic message being secure and sent with a MU2 EHR status including administrative control, wherein the universal resource locator in the electronic message is selectable by a user to access the information object via a web browser;

receiving, at the image sharing server and in response to the selection of the universal resource locator, a request for the information object based on the universal resource locator in the electronic message;

acquiring, by the image sharing server, the information object signified by the universal resource locator;

providing, by the image sharing server, the information object over a communications path for display on a web browser, wherein the providing of the information object over the communications path occurs over a different pathway or channel than the electronic message to avoid an attachment size limitation.

10. The method of claim 9, wherein the generating of the universal resource locator and sending of the secure electronic message with the universal resource locator occurs automatically in response to the receiving of the information object accompanied by the metadata.

11. The method of claim 9, further comprising:
receiving, over a second network, a request for the information object sent from a user device in response to an activation of the universal resource locator; retrieving the information object from the repository; and transmitting the information object to a browser of the user device over the second network.

12. The method of claim 11, further comprising transmitting a series of information objects in response to the request prompted by the activation of the universal resource locator.

13. The method of claim 9, wherein the information object is an image or a study.

14. The method of claim 9, wherein the electronic message is Direct Project (Direct) secure email message.

15. The method of claim 9, wherein the network includes a Digital Imaging Communications in Medicine (DICOM) network.

16. The method of claim 9, wherein the metadata accompanying the information object includes an application entity (AE) title.

17. The method of claim 9, further comprising:
receiving the electronic message at a first user device; and forwarding the universal resource locator to another recipient in a second secure electronic message.

18. A non-transitory computer readable information storage media having stored thereon instructions, that when executed by one or more processors cause to be performed a method for distributing information comprising:

receiving, over a network, an information object accompanied by metadata, the metadata identifying a trusted recipient;

storing the information object in a repository;

generating a universal resource locator for accessing the information object stored in the repository;

automatically mapping the metadata accompanying the information object to an electronic address of the trusted recipient;

automatically inserting the universal resource locator into a secure electronic message addressed to the electronic address of the trusted recipient;

sending the secure electronic message, using a secure email gateway, with the universal resource locator to the electronic address of the trusted recipient, the electronic message being secure and sent with a MU2 EHR status including administrative control, wherein the universal resource locator in the electronic message is selectable by a user to access the information object via a web browser;

receiving, in response to the selection of the universal resource locator, a request for the information object based on the universal resource locator in the electronic message;

acquiring the information object signified by the universal resource locator;

providing the information object over a communications path for display on a web browser, wherein the providing of the information object over the communications path occurs over a different pathway or channel than the electronic message to avoid an attachment size limitation.

19. The media of claim 18, further comprising wherein the computer readable program code that, if executed, generates the universal resource locator and the computer readable program code that, if executed, sends the secure electronic message with the universal resource locator execute automatically in response to receipt of the information object accompanied by the metadata.

20. The media of claim 18, further comprising:
receiving, over a second network, a request for the information object sent from a user device in response to an activation of the universal resource locator; retrieving the information object from the repository; and transmitting the information object to a browser of the user device over the second network.

21. The media of claim 20, further comprising transmitting a series of information objects in response to the request prompted by the activation of the universal resource locator.

22. The media of claim 18, wherein the information object is an image or a study.

23. The media of claim 18, wherein the electronic message is Direct Project (Direct) secure email message.

24. The media of claim 18, wherein the network includes a Digital Imaging Communications in Medicine (DICOM) network.

25. The media of claim 18, wherein the metadata accompanying the information object includes an application entity (AE) title.

26. The media of claim 18, further comprising:
receiving the electronic message at a first user device; and forwarding the universal resource locator to another recipient in a second secure electronic message.

* * * * *